United States Patent [19]

Chen et al.

[11] 4,251,632

[45] Feb. 17, 1981

[54] PREPARATION OF A BACTERIAL CELL AGGREGATE

[75] Inventors: Anthony H. Chen; Yun-Chi Jao, both of Elkhart, Ind.

[73] Assignee: Miles Laboratories, Inc., Elkhart, Ind.

[21] Appl. No.: 941,152

[22] Filed: Sep. 11, 1978

[51] Int. Cl.³ .................... C12N 11/08; C12P 19/24
[52] U.S. Cl. .................................. 435/180; 435/94; 435/233; 435/902
[58] Field of Search ............... 435/94, 174, 180, 182, 435/233, 902

[56] References Cited

U.S. PATENT DOCUMENTS 4,060,456  11/1977  Long ........................... 435/94

*Primary Examiner*—David M. Naff
*Attorney, Agent, or Firm*—Louis E. Davidson

[57] ABSTRACT

A shaped bacterial cell aggregate having increased hardness is produced by adding previously-produced dried finely-divided bacterial cell aggregate to bacterial cell aggregate subsequent to its formation but prior to its shaping.

6 Claims, No Drawings

PREPARATION OF A BACTERIAL CELL AGGREGATE

BACKGROUND AND PRIOR ART

Glucose isomerase is an enzyme that can be employed to catalyze the conversion of glucose (dextrose) to fructose (levulose). It is known that glucose isomerase can be produced by fermentation of certain organisms, such as *Streptomyces flavovirens, Streptomyces echinatur, Streptomyces achromogenus, Streptomyces albus, Streptomyces olivaceus, Bacillus coagulans* and the like, in appropriate nutrient media. The glucose isomerase is formed inside the bacterial cells which grow during its production. The cells can be filtered off from the fermentation beer and used directly as a source of glucose isomerase. Direct commercial use of such enzyme-containing bacterial cells had been hampered, however, by a major disadvantage. The enzyme activity was lost from the cells during use and thus the useful life of the cells was reduced. This disadvantage was overcome by the treatment of the bacterial cells with glutaraldehyde as described in U.S. Pat. No. 3,779,869. Additional techniques for immobilizing the enzyme activity in bacterial cells as well as for forming aggregates of such enzyme-containing bacterial cells are described, for example, in U.S. Pat. No. 3,821,086 and its U.S. Pat. Nos. Re. 29,130 and Re. 29,136 and in South African Pat. No. 73/5917. The above U.S. patents relate to use of certain anionic and cationic polyelectrolyte flocculating agents. The South African patent discloses various combinations of binders, reinforcing agents and cross-linking agents. While the above techniques provided bacterial cell aggregates which generally retained their enzyme activity during use, there was still a need to increase the hardness of the aggregates so that they could be commercially used in reactor beds of increasing depth. U.S. Pat. No. 3,935,069 describes the addition of certain metallic compounds in conjunction with polyelectrolyte flocculating agents to improve the hardness. However, this technique has limited utility.

A further development to improve the hardness of bacterial cell aggregates is described in copending U.S. Patent application Ser. No. 890,500, filed Mar. 27, 1978, which issued as U.S. Pat. No. 4,212,943, July 15, 1980, and assigned to the same assignee of this application. In Ser. No. 890,500 the mass of bacterial cells having desired enzymatic activity is treated with a cross-linking reaction product of (1) glutaraldehyde, cyanuric halide or combinations thereof and (2) a water-soluble cationic polymer obtained by the polymerization of an epihalohydrin with an alkylene polyamine, and then recovering the resulting aggregate. The resulting aggregates can be extruded or otherwise shaped to form shaped aggregates of improved hardness. However, when such shaped products are used in a column to conduct enzymatic processes, further hardness to reduce compaction losses is desirable.

In the manufacture of shaped bacterial cell aggregates, a certain amount of finely-divided product is produced having particle sizes too small for commercial use. Various techniques for utilizing these fines have been proposed. U.S. Pat. No. 4,060,456 discloses the recycling of product fines into a flocculation tank where a flocculant is employed to form bacterial cell aggregates. While this disclosure provides a use for recycled fines in the production of a flocculated aggregate, there is no indication as to any effect upon product hardness. Use of recycled enzyme supports is disclosed in U.S. Pat. Nos. 4,002,576; 4,078,970 and 4,087,330, but in no instance is there a disclosure or suggestion that such recycled materials can aid in improving shaped product hardness.

SUMMARY OF THE INVENTION

In accordance with the present invention, a process is provided for improving the hardness of a shaped bacterial cell aggregate which comprises adding previously produced dried finely-divided bacterial cell aggregate to bacterial cell aggregate subsequent to its formation but prior to its shaping. This invention is especially useful when the resulting aggregate is dried and then rehydrated for subsequent use.

DESCRIPTION OF THE INVENTION

The process of the present invention can be used with various enzyme-containing bacterial cells. The remainder of the disclosure will be directed at using the process with bacterial cells containing glucose isomerase activity.

The bacterial cells containing glucose isomerase activity useful in the process of the present invention can be produced by well-known procedures. The preferred enzyme-containing cells are produced by growing under submerged aerobic conditions a culture of *Streptomyces olivaceus* NRRL 3583 or mutants thereof in a medium containing appropriate nutrients. This is described in U.S. Pat. No. 3,625,828. The resulting bacterial cells are separated from the fermentation beer by filtration or centrifugation.

The bacterial cell aggregates used as starting materials in the process of the present invention can be produced by various well-known techniques. Such aggregates are preferably obtained by treating the above bacterial cells with glutaraldehyde in accordance with the procedure set forth in U.S. Pat. No. 3,779,869. The most preferred bacterial cell aggregates are obtained by treating the above bacterial cells with a cross-linking reaction product of (1) glutaraldehyde, cyanuric halide or combinations thereof and (2) a water-soluble cationic polymer obtained by the polymerization of an epihalohydrin with an alkylene polyamine. This procedure is described in copending U.S. application Ser. No. 890,500, filed Mar. 27, 1978, which issued as U.S. Pat. No. 4,212,943 on July 15, 1980. The following description relates to the production of bacterial cell aggregates employing the procedure of the above application Ser. No. 890,500.

The ingredients employed in the aggregation process are readily available. Glutaraldehyde and cyanuric halide, such as cyanuric trichloride, cyanuric tribromide, cyanuric triiodide and the like, are commercially available or can be produced by well-known techniques. The particular epihalohydrin-polyamine polymer used in this aggregation process is commercially available under the trademark BETZ 1180 from Betz Laboratories, Inc., Trevose, Penn. BETZ 1180 has a molecular weight less than one million, contains about 0.288 millimoles of amino groups per gram of solution (based on a ninhydrin assay) and is marketed as a solution containing 30 weight percent solids, based on total solution weight. This compound is disclosed in U.S. Pat. No. 3,915,904. The compound is described therein as a water-soluble cationic polymer obtained by the polymerization of an epihalohydrin with an alkylene polyamine having the formula $R_1R_2NRNH_2$ wherein R is a lower alkylene having from 2 to about 6 carbon atoms, and $R_1$ and $R_2$ are each a lower alkyl of from about 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity, and reacting the remaining portion of the epihalohydrin incrementally to obtain the cationic polymer, the temperature of polymerization being from about 60° C. to about 120° C. This material will hereinafter be referred to as the "polyamine polymer".

The cross-linking reaction product employed to form the bacterial cell aggregate can be one of three possible compositions. The polyamine polymer can be reacted with glutaraldehyde or cyanuric halide or with both glutaraldehyde and cyanuric halide.

The glutaraldehyde and/or cyanuric halide, which is collectively identified as component (1), is reacted with the polyamine polymer, which is identified as component (2), at a pH about 6 to 10 and at about 0° to 30° C. for about 0.5 to 2.5 hours. The overall cross-linking reaction product contains from about 12 to about 77 weight percent of component (1) and from about 23 to about 88 weight percent of component (2) based on the total weight of the active ingredients in components (1) and (2). The glutaraldehyde content of the reaction product is from about 0 to about 77 weight percent and the cyanuric halide content is from about 0 to about 22 weight percent based on the total weight of the active ingredients in components (1) and (2).

The reaction between glutaraldehyde and the polyamine polymer is preferably carried out at pH 8 to 9 and at about 18° to 25° C. for about 0.5 hour. The glutaraldehyde should be present in a molar ratio of at least one mole per mole of amino group in the polyamine polymer in order to avoid undesirable cross-linking of the polyamine polymer with glutaraldehyde.

The reaction between cyanuric halide alone and the polyamine polymer is preferably carried out at pH 8 to 9 and at 0° to 10° C. for about 1 to 2 hours. The cyanuric halide should be present in a molar ratio of at least one mole per mole of amino group in the polyamine polymer in order to avoid undesirable cross-linking of the polyamine polymer with cyanuric halide. Cyanuric halide, such as cyanuric trichloride, has three halogen reactive sites. One of these sites will react at 0° C. or higher. After reaction at the first site, the second site will react at 30° to 50° C. and the final site will react at 90° to 100° C. It is desirable to initially react only the first site on the cyanuric halide with the polyamine polymer. When the resulting cross-linking reaction product is subsequently reacted with the bacterial cells and heated to higher temperatures during drying, the remaining reactive sites on the cyanuric halide will then react with the polyamine polymer to provide additional cross-linking to the bacterial cell aggregate.

The reaction between the polyamine polymer and the combination of glutaraldehyde and cyanuric halide is carried out in steps. First, the cyanuric halide is reacted with the polyamine polymer at pH 8 to 9 and at 0° to 10° C. for about 1 to 2 hours. Preferably, in this situation the reactants have a mole ratio of one mole of cyanuric halide to two moles of amino groups on the polyamine polymer. An excess amount of glutaraldehyde is then added and the reaction is continued under the same pH and temperature conditions for about 0.5 hour.

The cross-linking reaction product employed in the production of the preferred bacterial cell aggregate is not a cationic polyelectrolyte, since the amino groups on the polyamine polymer which initially provided the cationic characteristic have been reacted with the glutaraldehyde and/or cyanuric halide and are thus no longer available.

Bacterial cell aggregates are prepared by contacting a mass of bacterial cells with the cross-linking reaction product prepared as described above at pH about 8 to 9 and at about 0° to 30° C. for about 0.5 to 1.5 hours. The cross-linking reaction product is employed in such amount and concentration that the bacterial cells are contacted with from about 4.5 to about 60 weight percent of the cross-linking reaction product active ingredients based upon the dry weight of the cells.

After the above reaction takes place, the resulting bacterial cell aggregate slurry is conveniently placed in a holding or surge tank upstream of filtration apparatus, such as a rotary vacuum filter. The slurry is then filtered to produce a filter cake of moist bacterial cell aggregate. This moist bacterial cell aggregate is then extruded or otherwise shaped into desirable shapes and then dried at about 60° C. for several hours.

The above-produced dried aggregate is ground and sized to produce desired aggregate particles having a size such as to pass through a 16 mesh screen and be retained on a 25 mesh screen (U.S. Screen sizes). The product material having a particle size larger than 16 mesh is reground while the product material having a particle size smaller than about 25 mesh and a moisture content of about 12 weight percent is recycled in accordance with the present invention.

The previously-produced dried finely-divided bacterial cell aggregate or fines which passed through the 25 mesh screen are added to the bacterial cell aggregate subsequent to its formation but prior to its shaping, such as by extrusion. This can be conveniently accomplished in at least two ways. In one procedure, the fines can be mixed with the bacterial cell aggregate slurry in the holding or surge tank upstream of the filter. In another procedure, the fines can be blended with the moist bacterial cell aggregate before it enters the extruder.

The dried finely-divided bacterial cell aggregate is added to the bacterial cell aggregate in an amount up to about 70 weight percent based on the total weight of the mixture solids. Preferably, the fines are added to the bacterial cell aggregate in an amount from about 5 to about 70 weight percent based on the total weight of the mixture solids. Most preferably, the fines are added in an amount of about 30 weight percent based on the total weight of the mixture solids.

The mixture of fines and moist bacterial cell aggregate is shaped, preferably by extruding such mixture through a die of reduced cross-sectional area, the shaped mixture or extrudate is dried and the dried aggregate is ground and separated to produce the desired particle size range. Any fines produced can be recycled in accordance with this invention. An extrusion die having openings of about ⅛-in. (3.18 mm) to about 1/16-in. (1.59 mm.) is presently preferred.

The resulting dried aggregate can be stored until subsequently needed for use in an enzymatic process. At that time the dried aggregate is rehydrated and conditioned for use. One illustrative conditioning process is described in U.S. Pat. No. 3,974,036.

A principal advantage of the present invention is an increase in the hardness of the bacterial cell aggregate after rehydration as compared to prior art bacterial cell aggregates. The hardness is expressed in relation to resistance to compression of the bacterial cell aggregate particles. An Instron Universal Tester Model 1102 was employed in a manner similar to that described in U.S. Pat. No. 3,935,069. This instrument is available from Instron Corporation, Canton, Mass.

The load or test cell employed with the above Instron Tester consists of a transparent acrylic plastic cylinder having an I.D. of 1.720 in. (4.37 cm.), an O.D. of 2.520 in. (6.45 cm.) and a height of 8.5625 in. (21.8 cm.). The bottom portion has a step 0.25 in. (0.635 cm.) thick with an opening of 1.5 in. (3.81 cm.) to form a support for a micro-filter. A convenient micro-filter is a spinnerette employed in textile spinning having 14,500 openings about 0.008 in. (0.2032 mm.) dia.

A Type 304 stainless steel plunger 1.693 in. (4.3 cm.) dia. and 5.375 in. (13.66 cm.) long is mounted so as to move coaxially into the above cylinder. Appropriate indicia are located along the load cell to show a sample depth of 4 in. (10.17 cm.). Provisions are also made for applying a reduced pressure or vacuum to the bottom of the load cell and for collecting any liquid which passes through the micro-filter.

If a sample of bacterial cell aggregate is placed in the above load cell and pressure is applied to the sample through the plunger, the sample will be compressed. The pressure needed to compress the sample a given amount is an indication of the sample hardness.

The following is the Rehydration Hardness Assay Procedure employed in the examples of this specification:

A 33 weight percent aqueous solution of glucose is adjusted to pH 8.1. A 130 g. portion of dried bacterial cell aggregate is mixed with 1300 ml. of such glucose solution with gentle agitation at 24° C. for one hour. The resulting mixture is drained over a 20 mesh screen (U.S. sieve size) for about 30 seconds. The solids are then resuspended in a fresh portion of the above glucose solution and stirred for 5 minutes at 24° C. The resulting slurry is allowed to settle for 5 minutes and then is drained as above. The solids are then resuspended in a fresh portion of the above glucose solution and stirred for 5 minutes at 24° C. Approximately half of the resulting slurry is then poured into the test cell to a height of 4 in. (10.17 cm.). A reduced pressure or vacuum of 1-in. (2.54 cm.) of mercury is applied to the bottom of the test cell for three minutes to suck liquid through the micro-filter. The plunger is then lowered until it just touches the top of the sample. The crosshead on the Instron instrument is attached to the plunger and is set to move downward at a speed of 0.5 in./min. (1.27 cm./min.) and to stop at a penetration of 1-in. (2.54 cm.). The recording chart speed is set at 5-in./min (12.7 cm./min.). At the end of the penetration, the plunger is allowed to recover for exactly one minute. The plunger is again placed in contact with the top of the sample and the Instron is set to stop at a penetration of 1-in. (2.54 cm.). The pressure necessary to achieve the second penetration is the measure of the sample hardness.

The invention is described in further detail in the following illustrative examples.

EXAMPLE 1

A solution of polyamine polymer was prepared by diluting 1750 g. of BETZ 1180 solution containing 525 g. of active material with distilled water to form 15 liters. The pH was adjusted to 9. A solution of glutaraldehyde was prepared by diluting 2670 ml. of 25 weight percent glutaraldehyde containing 667 g. active material with distilled water to form 15 liters. The pH was adjusted to 9. These two solutions were then mixed and distilled water was added to form a total of 42 liters. The reaction took place at a pH of about 9 and a temperature of about 25° C. for about 0.5 hour. The resulting product was formed from a reaction mixture containing 56 weight percent glutaraldehyde and 44 weight percent polyamine polymer based on the total weight of the glutaraldehyde (Component 1) and the polyamine polymer (Component 2).

A culture of a mutant of *Streptomyces olivaceus* NRRL 3583 was grown in an agitated aerated fermentor containing an appropriate nutrient medium described in U.S. Pat. No. 3,625,828. The resulting fermentor broth containing a mass of bacterial cells was adjusted to pH 8-9 by addition of appropriate buffering materials. The above-prepared solution was added to the fermentor broth in an amount of 6 ml. per gram of dry cell weight to provide 17 weight percent total reaction product based on the dry weight of the bacterial cells. After about 30 min. reaction time at 25° C. and pH 8-9, the treated broth containing the bacterial cell aggregate was placed in a holding tank from which it then passed to a rotary vacuum filter. The resulting wet filter cake was cut into small pieces about 1 sq. cm. in a chopper. The chopped moist filter cake pieces having a moisture content of about 76 weight percent were then divided into four portions. One portion was then extruded through a die having six ⅛-in. (3.18 mm.) dia. openings using a non-compression extruder screw with 100 RPM screw rotation. The resulting extruded bacterial cell aggregate was then dried at 60° C. for 4 to 6 hours and milled. The milled particles were then separated to collect the desired fraction which passes through a 16 mesh screen but which is retained on a 25 mesh screen. The fines which passed through the 25 mesh screen were collected for further use. The −16+25 fraction was designated as the "Control". Its glucose isomerase activity was measured by the assay method set forth in U.S. Pat. No. 3,779,869 to be 430 glucose isomerase units (G.I.U.) per gm. Its hardness was also measured in the above-described Rehydration Hardness Assay Procedure.

The remaining three portions of moist bacterial cell aggregate filter cake were then individually mixed in a blender with controlled amounts of previously-prepared dried *Streptomyces olivaceus* bacterial cell aggregate having a particle cell of less than about 25 mesh and having a moisture content of 12 weight percent. Each of the three mixed portions (Samples 1B, 1C and 1D) were then individually extruded, dried, milled and separated as described above for the Control to produce portions of bacterial cell aggregate having particle sizes which pass through a 16 mesh screen and are retained on a 25 mesh screen. The hardness and enzyme activity of each portion product were then obtained. The results are shown in the below Table I.

The hardness of the samples is expressed as a percentage increase over the hardness of the Control.

TABLE I

| Sample | Overall Moisture Content Wt.Percent | Weight Percent Based on Total Solids | | Percent Increased Hardness | Activity G.I.U./gm. |
| --- | --- | --- | --- | --- | --- |
| | | Recycled Fines | Filter Cake | | |
| 1A (Control) | 76.0 | 0 | 100 | — | 430 |
| 1B | 69.5 | 28.1 | 71.9 | 42.46 | 459 |
| 1C | 56.5 | 60.1 | 39.9 | 49.01 | 433 |
| 1D | 43.5 | 77.9 | 22.1 | 133.15 | 231 |

The reduction in enzyme activity for Sample 1D is believed due to inactivation caused by elevated temperature and pressure created in the extruder by the lower moisture content. It appears that an addition of fines up to about 70 weight percent based on total solids can be used without impairing the enzyme activity.

EXAMPLE 2

The procedure of Example 1 was repeated with the following changes. Three portions of the moist filter cake were individually mixed with 46.8 weight percent recycled bacterial cell aggregate fines based on total solids. These three portions were then separately extruded through dies having six openings of ⅛-in. (3.18 mm.) dia., eight openings of 1/16-in. (1.59 mm.) dia. and ten openings of 3/64-in. (1.19 mm.) dia. The results are shown in the following Table II.

TABLE II

| Sample | Moisture Content Wt. Percent | Weight Percent Based On Total Solids | | Die Dia. Inch | Percent Increased Hardness | Activity G.I.U./gm. |
| --- | --- | --- | --- | --- | --- | --- |
| | | Recycled Fines | Filter Cake | | | |
| 2A (Control) | 80.32 | 0 | 100 | ⅛ | — | 576 |
| 2B | 73.87 | 46.8 | 53.2 | ⅛ | 36.22 | 542 |
| 2C | 73.87 | 46.8 | 53.2 | 1/16 | 53.58 | 557 |
| 2D | 73.87 | 46.8 | 53.2 | 3/64 | 14.82 | 533 |

The preferred die dia. of ⅛-in. (3.18 mm.) to 1/16-in. (1.59 mm.) provides a desirable high increase in hardness with no corresponding loss in activity.

EXAMPLE 3

The procedure of Example 1 was repeated with the following changes. Three portions of the moist filter cake were individually mixed with 60.1 weight percent recycled bacterial cell aggregate fines based on total solids. All four portions were then extruded through eight 1/16-in. (1.59 mm.) dia. openings. The Control portion (Sample 3A) was extruded using a non-compression screw rotating at 60 RPM. A first portion (Sample 3B) mixed with the fines was extruded under the same conditions as the Control. A second portion (Sample 3C) mixed with the fines was extruded using a single flight 3:1 compression screw at 40 RPM. A third portion (Sample 3D) mixed with the fines was extruded using a double flight 3:1 compression screw at 30 RPM. The results are shown in the following Table III.

TABLE III

| Sample | Moisture Content Wt. Percent | Weight Percent Based On Total Solids | | Percent Increased Hardness | Activity G.I.U./gm. |
| --- | --- | --- | --- | --- | --- |
| | | Recycled Fines | Filter Cake | | |
| 3A (Control) | 78.30 | 0 | 100 | — | 650 |
| 3B | 58.11 | 60.1 | 39.9 | 114.58 | 506 |
| 3C | 58.11 | 60.1 | 39.9 | 117.20 | 517 |
| 3D | 58.11 | 60.1 | 39.9 | 178.01 | 484 |

All of the samples employing recycled fines had desirable increases in hardness with acceptable levels of retained activity.

EXAMPLE 4

The procedure of Example 1 was repeated with the following changes. One portion (Sample 4B) of the moist filter cake was mixed with 46.8 weight percent recycled bacterial cell aggregate fines based on total solids. Another portion (Sample 4C) was dried at 60° C. for 10 min. prior to extrusion. A further portion (Sample 4D) was dried at 60° C. for 20 min. prior to extrusion. Still another portion (Sample 4E) was dried at 60° C. for 30 min. prior to extrusion. A final portion (Sample 4F) was dried at 60° C. for 40 min. prior to extrusion. The untreated Control portion (Sample 4A) and the other treated portions were all extruded through eight 1/16-in. (1.59 mm.) dia. openings using a non-compression screw at 80 RPM. The results are shown in the following Table IV.

TABLE IV

| Sample | Moisture Content Wt. Percent | Weight Percent Based On Total Solids | | Percent Increased Hardness | Activity G.I.U./gm. |
| --- | --- | --- | --- | --- | --- |
| | | Recycled Fines | Filter Cake | | |
| 4A (Control) | 74.36 | 0 | 100 | — | 440 |
| 4B | 61.69 | 46.8 | 53.2 | 58.14 | 440 |
| 4C | 68.90 | 0 | 100 | −21.65 | 446 |
| 4D | 67.20 | 0 | 100 | 2.29 | 465 |
| 4E | 65.10 | 0 | 100 | 9.22 | 471 |
| 4F | 57.00 | 0 | 100 | 18.37 | 452 |

It can be seen from the above data that merely drying the filter cake, without adding recycled fines, cannot achieve the increased hardness produced by the controlled addition of the fines.

All the above examples added the recycled fines to the moist filter cake just prior to extrusion. The following example describes the effect of adding the recycled fines to the bacterial cell aggregate prior to filtration.

EXAMPLE 5

The procedure of Example 1 was followed to produce a slurry of bacterial cell aggregate in the holding tank prior to the filter. Recycled fines of bacterial cell aggregate were then added to one portion of the tank contents in an amount of 30 weight percent based on the total solids. The resulting mixture as well as the untreated portion were separately filtered, extruded through eight 1/16-in. (1.59 mm.) dia. holes using a non-compression screw at 80 RPM, dried, milled and separated according to Example 1. The treated portion having the recycled fines had hardness 45.15 percent greater than the untreated Control. It can thus be seen that addition of recycled fines of bacterial cell aggregate subsequent to formation and prior to extrusion of a bacterial cell aggregate can significantly improve the hardness of the resulting shaped aggregate particles.

The bacterial aggregates produced in the manner described above were all capable of converting glucose to fructose. The glucose isomerase activity was not impaired through the use of this novel process.

What is claimed is:

1. A process for producing an extruded Streptomyces olivaceus bacterial cell aggregate having improved hardness which comprises forming a bacterial cell aggregate by contacting a mass of Streptomyces olivaceus bacterial cells for 0.5 to 1.5 hours with a cross-linking reaction product of (1) a material selected from the class consisting of glutaraldehyde, cyanuric halide and combinations thereof and (2) a water-soluble cationic polymer obtained by the polymerization of an epihalohydrin with an alkylene polyamine having the formula $R_1R_2NRNH_2$ wherein R is a lower alkylene having from 2 to about 6 carbon atoms, and $R_1$ and $R_2$ are each a lower alkyl of from 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity, and reacting the remaining portion of the epihalohydrin incrementally to obtain the cationic polymer, the temperature of polymerization being from about 60° C. to about 120° C., adding to said bacterial cell aggregate a portion of previously-produced dried finely-divided bacterial cell aggregate of the same overall composition to form a bacterial cell aggregate mixture, extruding such mixture through a die of reduced cross-sectional area, drying the extrudate, and grinding and separating the extrudate to produce the desired particle size range.

2. A process according to claim 1 wherein the dried finely-divided bacterial cell aggregate has a particle size smaller than about 25 mesh.

3. A process according to claim 1 wherein the dried finely-divided bacterial cell aggregate is added to the bacterial cell aggregate in an amount up to about 70 weight percent based on the total weight of the mixture solids.

4. A process according to claim 1 wherein the dried finely-divided bacterial cell aggregate is added to the bacterial cell aggregate in an amount from about 5 to about 70 weight percent based on the total weight of the mixture solids.

5. A process according to claim 1 wherein the dried finely-divided bacterial cell aggregate is added to the bacterial cell aggregate in an amount of about 30 weight percent based on the total weight of the mixture solids.

6. A process according to claim 1 wherein the cross-linking product results from the reaction of from about 12 to about 77 weight percent of component (1) and from about 23 to about 88 weight percent of component (2) based on the total weight of the active ingredients in components (1) and (2).

* * * * *